United States Patent [19]

Heitsch et al.

[11] Patent Number: 5,374,731

[45] Date of Patent: Dec. 20, 1994

[54] AMINO ACID DERIVATIVES WITH RENIN-INHIBITING PROPERTIES, A PROCESS FOR THE PREPARATION THEREOF, AGENTS CONTAINING THESE, AND THE USE THEREOF

[75] Inventors: Holger Heitsch, Hofheim am Taunus; Rainer Henning, Hattersheim am Main; Wolfgang Linz, Kelkheim/Taunus; Wolf-Ulrich Nickel, Bad Soden am Taunus; Dieter Ruppert; Hansjörg Urbach, both of Kronberg/Taunus, all of Germany

[73] Assignee: Hoechst Aktiengesellschaft, Frankfurt am Main, Germany

[21] Appl. No.: 579,695

[22] Filed: Sep. 10, 1990

[30] Foreign Application Priority Data

Sep. 12, 1989 [DE] Germany ............... 3930397
Oct. 4, 1989 [DE] Germany ............... 3933096

[51] Int. Cl.$^5$ ............... C07D 401/12; A61K 31/455; A61K 31/445
[52] U.S. Cl. ............... 546/194
[58] Field of Search ............... 546/194; 514/318

[56] References Cited

U.S. PATENT DOCUMENTS

| | | | |
|---|---|---|---|
| 4,855,286 | 8/1989 | Wagner et al. | 514/19 |
| 5,055,466 | 10/1991 | Weller, III et al. | 546/194 |
| 5,116,835 | 5/1992 | Rüger et al. | 546/194 |

FOREIGN PATENT DOCUMENTS

| | | |
|---|---|---|
| 0184855 | 6/1986 | European Pat. Off. . |
| 0189203 | 7/1986 | European Pat. Off. . |
| 0202577 | 11/1986 | European Pat. Off. . |
| 0229667 | 7/1987 | European Pat. Off. . |
| 0230266 | 7/1987 | European Pat. Off. . |
| 0237202 | 9/1987 | European Pat. Off. . |
| 0255082 | 2/1988 | European Pat. Off. . |
| 0310071 | 4/1989 | European Pat. Off. . |
| 0310072 | 4/1989 | European Pat. Off. . |
| 0329013 | 8/1989 | European Pat. Off. . |
| 0417698-A2 | 3/1991 | European Pat. Off. ........ 546/194 |
| WO87/05302 | 9/1987 | WIPO . |
| WO88/05050 | 7/1988 | WIPO . |

*Primary Examiner*—C. Warren Ivy
*Assistant Examiner*—D. Margaret M. Mach
*Attorney, Agent, or Firm*—Finnegan, Henderson Farabow, Garrett & Dunner

[57] ABSTRACT

Amino acid derivatives with renin-inhibiting properties, a process for the preparation thereof, agents containing these, and the use thereof The invention relates to renin-inhibiting amino acid derivatives of the formula

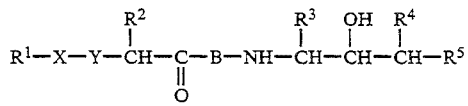

in which $R^1$ is a radical of a substituted nitrogen-containing heterocycle such as piperidine, X is CO, CS, $SO_2$ or SO, Y is $CH_2$, O or S, B is the radical of an amino acid of the formula H—B—OH, and $R^3$, $R^4$ and $R^5$ are as defined in the description, a process for the preparation thereof, agents containing these, and the use thereof.

4 Claims, No Drawings

AMINO ACID DERIVATIVES WITH RENIN-INHIBITING PROPERTIES, A PROCESS FOR THE PREPARATION THEREOF, AGENTS CONTAINING THESE, AND THE USE THEREOF

EP-A-184,855, EP-A-189,203, EP-A-202,577, EP-A-299,655, EP-A-230,266, EP-A-237,202, EP-A-310,071, EP-A-310,072, WO-A-87/05302 and WO 88/05050 disclose amino diol derivatives with a renin-inhibiting action.

Renin inhibitors are furthermore described in Biochem. Biophys. Res. Comm. 132, 155–161 (1985), in Biochem. Biophys, Res. Comm. 146, 959–963 (1987), in FEBS Lett. 230, 38–42 (1988), in J. Med. Chem. 30, 976 (1987) and J. Med. Chem. 31, 2277 (1988).

It has now been found that acyl-aminoacyl-substituted amino diol derivatives which are azacyclic at the N terminus and have heterocyclic substitution at the C terminus are, surprisingly, exceptionally highly active and highly specific renin inhibitors which have a considerably improved absorption and considerably extended duration of action in vivo.

Hence the invention relates to compounds of the formula

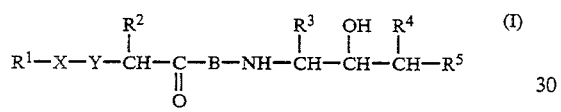

in which $R^1$ is a radical of the formula II, III or IV

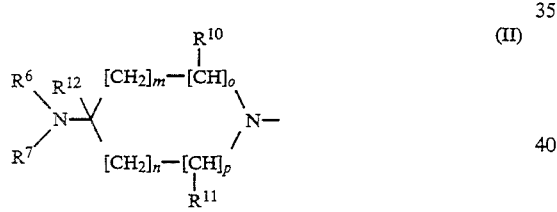

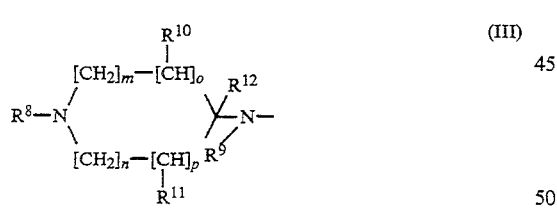

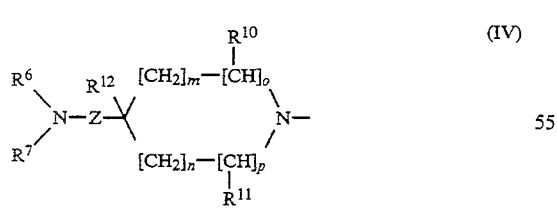

in which $R^6$ and $R^7$ are identical or different and are
hydrogen,
an optionally substituted aliphatic radical having 1-21 carbon atoms,
an optionally substituted alicyclic radical having 3-20 carbon atoms,
an optionally substituted alicyclic-aliphatic radical having 4-20 carbon atoms,
an optionally substituted aromatic radical having 6-12 carbon atoms,
an optionally substituted araliphatic radical having 7-32 carbon atoms,
an optionally substituted heteroaromatic or heteroaromatic-$(C_1-C_8)$-aliphatic radical having 5-12 ring atoms in each case,
or, wherein not yet embraced by the abovementioned definitions, are
an optionally substituted alkanoyl radical having 1-18 carbon atoms,
an optionally substituted $(C_3-C_8)$-cycloalkyl-$(C_1-C_8)$-alkanoyl radical,
an optionally substituted $(C_7-C_{13})$-aroyl radical,
an optionally substituted heteroaroyl radical,
an optionally substituted $(C_8-C_{12})$-aryl-$(C_1-C_{18})$-alkaloyl radical,
an optionally substituted heteroaryl-$(C_1-C_{18})$-alkanoyl radical or
an optionally substituted $(C_8-C_{12})$-aryl-$(C_1-C_4)$-alkoxy-carbonyl radical, or $R^6$ and $R^7$ form, together with the nitrogen atom carrying them, a 4- to 8-membered ring which can be saturated or unsaturated and can contain another hetero atom selected from the group nitrogen, oxygen and sulfur;
or
$R^6$ is as defined above and $R^7$ is
amino,
optionally substituted $(C_1-C_4)$-alkylamino,
optionally substituted di-$(C_1-C_4)$-alkylamino,
hydroxyl,
optionally substituted $(C_1-C_4)$-alkoxy,
optionally substituted $(C_1-C_4)$-alkylsulfonyl,
optionally substituted $(C_6-C_{12})$-arylsulfonyl or carbamoyl;
$R^8$ has the meaning stated for $R^6$ or $R^7$;
$R^9$ is
hydrogen, $C_1-C_8$-alkyl, $(C_3-C_8)$-cycloalkyl, $(C_3-C_8)$-cycloalkyl-$(C_1-C_4)$-alkyl,
optionally substituted $(C_6-C_{12})$-aryl,
optionally substituted $(C_7-C_{13})$-aralkyl;
$R^{10}$, $R^{11}$ and $R^{12}$ are identical or different and are hydrogen or $(C_1-C_6)$-alkyl, or $R^{10}$ and $R^{11}$ together form a $(C_2-C_4)$-alkanediyl bridge, preferably ethylene bridge, and $R^{12}$ is as defined above;
m is 0, 1, 2 or 3;
n is 1, 2, 3 or 4;
o is 0, 1, 2 or 3;
p is 1, 2, 3 or 4;
X is —CO—, —CS—, —SO$_2$— or —SO—;
Y is —(CH$_2$)$_1$—(CR$^{13}$R$^{14}$)$_r$—, —O— or —S—, in which
q is 0, 1, 2 or 3,
r is 0, 1 or 2;
Z is a branched or unbranched aliphatic radical having 1-6 carbon atoms, preferably $(C_1-C_6)$-alkanediyl, and
$R^{13}$ and $R^{14}$ are identical or different and are hydrogen or $(C_1-C_6)$-alkyl;
$R^2$ is hydrogen, $C_1-C_{10}$)-alkyl, $(C_6-C_{12})$-aryl, $(C_5-C_{12})$-aryl-$(C_1-C_4)$-alkyl, $(C_3-C_8)$-cycloalkyl, $(C_3-C_8)$-cycloalkyl-$(C_1-C_4)$-alkyl, heteroaryl or heteroaryl-$(C_1-C_4)$-alkyl, it being possible for aryl and heteroaryl to be substituted by one or two identical or different radicals from the series halogen, hydroxyl, $(C_1-C_4)$-alkoxy, amino, $(C_1-C_4)$- alkylamino, di-($C_1$–$C_4$)-alkylamino, $CF_3$ and ($C_1$–$C_4$)-alkyl;

$R^3$ is hydrogen, ($C_1$–$C_{10}$)-alkyl, ($C_3$–$C_8$)-cycloalkyl, ($C_3$–$C_8$)-cycloalkyl-($C_1$–$C_4$)-alkyl, ($C_6$–$C_{12}$)-aryl or ($C_6$–$C_{12}$)-aryl-$C_1$–$C_4$)-alkyl;

$R^4$ is hydrogen, ($C_1$–$C_{10}$)-alkyl, ($C_6$–$C_{12}$)-aryl, ($C_6$–$C_{12}$)-aryl-($C_1$–$C_4$-alkyl, hydroxyl or amino;

$R^5$ is a radical of the formula II:

$$(CH_2)_x\text{—}CHR^{15}\text{—}Het \qquad (II)$$

where $R^{15}$ is hydrogen, ($C_1$–$C_7$)-alkyl, ($C_1$–$C_4$)-alkoxy, ($C_1$–$C_4$)-alkylthio, ($C_1$–$C_4$)-alkylamino, hydroxyl, azido or halogen, and Het is a 5- to 7-membered heterocyclic ring which can be benzo-fused, aromatic, partially hydrogenated or completely hydrogenated, which can contain as hetero atoms one or two identical or different radicals from the group comprising N, O, S, NO, SO, $SO_2$, and which can be substituted by one or two identical or different radicals from the series ($C_1$–$C_4$)-alkyl, allyl, ($C_1$–$C_4$)-alkoxy, hydroxyl, halogen, amino, mono- or di-($C_1$–$C_4$)-alkylamino and $CF_3$; and s is 0, 1, 2, 3 or 4; and B is the radical of an amino acid H—B—OH, preferably from the series phenylalamini, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valien, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalamnine, 2-naphthylalanine, 4-nitrophenylalanine, norvaline, β-2-benzo[b]thienylalanine, β-3-benzo[b]-thienylalanine, 2-fluorophenylalanine, 3-fluorophenylalanine, 4-pyridylalanine, 4-fluorophenylalanine, norleucine, cysteine, S-methylcysteine, 1,2,3,4-tetrahydroisoquinoline-3-carboxylic acid, homophenylalanine, DOPA, O-timentyl-DOPA, N-methylhistidine, 2-amino-4-(2-thienyl)-butyric acid, 2-amino-4-(3-thienyl)butyric acid, 3-(2-thienyl)serine, 2- and 4-thiazolyalanine, (Z)-dehydrophenylalanine, (E)-dehydrophenylalanine, 1,3-dioxolan-2-ylalanine, N-pyrrolyalanline and 1-, 3- or 4-pyrazolylalanine, and the physiologically tolerated salts thereof.

The centers of chirality in the compounds of the formula I can have the R or S or R,S configuration, B is preferably in the S configuration or, in the case of cysteine and amino acids derived therefrom, in the R configuration.

An aliphatic radical is preferably an alkyl radical or a corresponding unsaturated radical. The radical can be straight-chain or branched. A corresponding statement applies to radicals derived therefrom, such as, for example, alkoxy, alkylthio, alkylamino, dialkylamino, alkanoyl and aralkyl.

An alicyclic radical is, for example, cycloalkyl or a radical derived therefrom (cf. alkyl). ($C_3$–$C_8$)-cycloalkyl preferably means cyclopropyl, cyclobutyl, cyclopentyl, cyclohexyl, cycloheptyl and cyclooctyl. If these cyclic radicals carry more than one substituent, the latter can be both cis and trans with respect to one another. An alicyclic-aliphatic radical means, for example, cycloalkylalkyl and radicals derived therefrom (cf. alkyl).

An aromatic radical is preferably ($C_6$–$C_{12}$-aryl such as, for example, phenyl, naphthyl or biphenylyl; phenyl is preferred.

A corresponding statement applies to radicals derived therefrom, such as, for example, aryloxy, aroyl, aralkyl and aralkoxy.

Araliphatic radicals are, inter alia, aralkyl radicals, by which is preferably means an unsubstituted or substituted ($C_6$–$C_{12}$)-aryl radical which is linked to ($C_1$–$C_6$)-alkyl, such as, for example, benzyl, α- and β-naphthylmethyl, halobenzyl and alkoxybenzyl, but aralkyl is not restricted to the said radicals.

A heteroaromatic radical means, in particular, a radical which contains a six-membered aromatic ring which is derived from benzene and in which one or more CH groups are replaced by N, or which contains a five-membered aromatic ring which is derived from benzene and in which two CH groups are replaced by S, NH or N and in which further CH groups are optionally replaced by N. This heteroaryl radical is preferably monocyclic or bicyclic, being fused in the latter case to a benzene or to a five- or six-membered ring as defined above. Corresponding statements apply to radicals derived therefrom, such as the heteroaromatic-aliphatic radicals heteroaralkyl, heteroaroyl, or to heteroaryloxy.

A Het radical within the meaning of the above definition is, for example, a heteroaryl radical such as pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzo-fused, cyclopenta-, cyclohexa- or cyclohepta-fused derivative of these radicals. This heterocyclic can be up to trisubstituted onone nitrogen atom by oxy, ($C_1$–$C_6$-alkyl, for example methyl or ethyl, phenyl or phenyl-($C_1$–$C_4$)-alkyl, for example benzyl, and/or on one or more carbon atoms by ($C_1$–$C_4$)-alkyl, for example methyl, phenyl, phenyl-($C_1$–$C_4$)-alkyl, for example benzyl, halogen, for example chlorine, hydroxyl, ($C_1$–$C_4$)-alkoxy, for example methoxy, phenyl-($C_1$–$C_4$)-alkoxy, for example benzyloxy, or oxo, and can be partially saturated and is, for example, 2- or 3-pyrrolyl, phenylpyrrolyl, for example 4- of 5-phenyl-2-pyrrolyl, 2-furyl, 2-thienyl, 4-imidazolyl, methyl-imidazolyl, for example 1-methyl-2-, 4- or 5-imidazolyl, 1,3-thiazol-2-yl, 2-, 3- or 4-pyridyl, 1-oxy-2-, 3- or 4-pyridyl, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4-quinolyl, 4-hydroxy-2-quinolyl, 1-, 2- or 4-isoquinolyl, 1-oxo-1,2-dihydro-3-isoquinolyl, 2-quinoxalinyl, 2-benzofuranyl, 2-benzoxazolyl, 2-benzothiozolyl, benzo[e]indol-2-yl or β-carbolin-3-yl.

Partially hydrogenated or completely hydrogenated heterocyclic rings are, for example, dihydropyridinyl, pyrrolidinyl, for example, 2-, 3- or 4-N-methylpyrrolidinyl, piperidinyl, piperazinyl, morpholino, thiomorpholino, tetrahydrothienyl.

Halogen is fluorine, chlorine, bromine or iodine.

(m+n) is preferably ≧2.

(o+p) is preferably ≧1.

(q+r) is preferably ≧1.

s is preferably ≧1.

The term "optionally substituted" used in the introduction means (unless specifically defined otherwise hereinafter) that the relevant radical can be substituted by one, two or three, preferably one or two, identical or different radicals from the series $(C_1-C_5)$-alkyl, $(C_1-C_5)$-alkoxy, hydroxyl, halogen, $(C_1-C_6)$-alkanoyl, $CF_3$, amino, $(C_1-C_6)$-alkylamino, di-$(C_1-C_6)$-alkylamino, carbamoyl, $(C_1-C_6)$-alkoxycarbonyl and sulfamoyl.

Salts of compounds of the formula I mean, in particular, pharmaceutically utilizable or non-toxic salts.

Salts of these types are formed, for example, by compounds of the formula I which contain acidic groups, for example carboxyl, with alkali metals or alkaline earth metals, such as Na, K, Mg and Ca, as well as with physiologically tolerated organic amines such as, for example, triethylamine and tri(2-hydroxyethyl)amine.

Compounds of the formula I which contain basic groups, for example an amino group or a guanidino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid.

Preferred compounds of the formula I are those in which $R^6$ and $R^7$ are identical or different and are hydrogen, $(C_1-C_{18})$-alkyl,
an aliphatic acyclic radical of the formula $C_aH_{(2a-b+1)}$ in which double bonds are not, if their number exceeds 1, cumulative, a is an integer from 2 to 18 and b is an even number from 2 to a, a mono-, di- or tricyclic, non-aromatic, optionally branched hydrocarbon radical of the formula $C_cH_{(2c-d+1)}$ in which c is an integer from 3 to 20 and d is an even number from 0 to (c−2),
$(C_6-C_{12})$-aryl which is optionally substituted by one or two identical or different radicals from the series $(C_1-C_4)$-alkyl, $(C_1-C_4)$-alkoxy, hydroxyl, halogen, amino, $(C_1-C_4)$-alkylamino, di-$(C_1-C_4)$-alkylamino and $CF_3$,
$(C_6-C_{12})$-aryl-$(C_1-C_8)$-alkyl or $(C_7-C_{13})$-aroyl-$(C_1-C_8)$-alkyl, each of which can be substituted in the aryl moiety as described above,
mono- or bicyclic, optionally partially hydrogenated heteroaryl, heteroaryl-$(C_1-C_8)$-alkyl or heteroaryl-$(C_1-C_8)$-alkanoyl with 5–7 or 8–10 ring atoms in each case, of which up to 9 ring atoms are carbon and 1 to 2 ring atoms are sulfur or oxygen and/or 1 to 4 ring atoms are nitrogen, which can be substituted in the heteroaryl moiety as described above for aryl,
$(C_1-C_{18})$-alkanoyl,
$(C_5-C_{12})$-aryl-$(C_1-C_8)$-alkanoyl which can be substituted in the aryl moiety as described above,
$(C_7-C_{13})$-aroyl-$(C_1-C_5)$-alkanoyl which can be substituted in the aryl moiety as described above,
$(C_1-C_6)$-alkoxycarbonyl-$(C_1-C_8)$-alkanoyl,
$(C_6-C_{12})$-aryloxycarbonyl-$(C_1-C_8)$-akanoyl which can be substituted in the aryl moiety as described above,
$(C_6-C_{12})$-aryl-$(C_1-C_8)$-alkoxycarbonyl,
$(C_1-C_6)$-alkoxy-$(C_1-C_6)$-alkanoyl,
$(C_6-C_{12})$-aryloxy-$(C_1-C_6)$-alkanoyl which can be substituted in the ary moiety as described above for aryl,
$(C_1-C_6)$-acyl-$(C_1-C_8)$-alkanoyl,
carboxy-$(C_1-C_4)$-alkanoyl
carbamoyl-$(C_1-C_4)$-alkanoyl,
amino-$(C_1-C_4)$-alkyl,
$(C_1-C_4)$-alkanoylamino-$(C_1-C_4)$-alkyl,
$C_7-C_{13})$-aroylamino-$(C_1-C_4)$-alkyl,
$(C_1-C_4)$-alkoxycarbonylamino-$(C_1-C_4)$-alkyl,
$(C_6-C_{12})$-aryl-$(C_1-C_4)$-alkoxycarbonylamin-$(C_1-C_4)$-alkyl,
$(C_6-C_{12})$-aryl-$(C_1-C_4)$-alkylamino-$(C_1-C_4)$-alkyl,
$(C_1-C_4)$-alkylamino-$(C_1-C_4)$-alkyl,
di-$(C_1-C_4)$-alkylamino-$(C_1-C_4)$-alkyl,
guanidino-$(C_1-C_4)$-alkyl, p2 $(C_1-C_4)$-alkylthio-$(C_1-C_4)$-alkyl,
$C_6-C_{12})$-arylthio-$(C_1-C_4)$-alkyl which can be substituted in the aryl moiety as described above,
carboxy-$(C_1-C_4)$-alkyl, carbamoyl-$(C_1-C_4)$-alkyl,
$(C_1-C_4)$-alkoxycarbonyl-$(C_1-C_4)$-alkyl,
$(C_6-C_{12})$aryloxy-$(C_1-C_4)$-alkyl which can be substituted in the aryl moiety as described above for aryl, or $R^5$ and $R^7$ form, together with the nitrogen atom carrying them, a 5- or 6-membered ring which can be saturated or unsaturated and can contain a further hetero atom selected from the group comprising nitrogen, oxygen and sulfur;

or $R^6$ is as defined above, and
$R^7$ is amino, $(C_1-C_4)$-alkylamino, di-$(C_1-C_4)$-alkylamino, hydroxy, $(C_1-C_4)$-alkoxy, $(C_1-C_4)$-alkylsulfonyl, $C_6-C_{12})$-arylsulfonyl or carbamoyl;
$R^8$ has the meaning stated for $R^6$ or $R^7$;
$R^9$ is hydrogen, $(C_1-C_5)$-alkyl, $(C_4-C_6)$-cycloalkyl, $(C_4-C_5)$-cycloalkyl$(C_1-C_4)$-alky, $(C_6-C_{12})$-aryl or $(C_6-C_{12})$-aryl-$(C_1-C_2)$-alkyl;
$R^{10}$, $R^{11}$ and $R^{12}$ are identical or different and are hydrogen or $(C_1-C_4)$-alkyl;
m is 0, 1, 2 or 3;
n is 1, 2 or 3;
o is 0, 1, 2 or 3;
p is 0, 1, 2 or 3;
X is —CO—, —CS—, —SO$_2$— or —SO—;
Y is —(CH$_2$)$_q$—(CR$^{13}$R$^{14}$)$_r$—, —O— or —S—, in which
q is 0, 1, 2 or 3,
r is 0, 1 or 2;
Z is a branched or unbranched aliphatic radical having 1–4 carbon atoms, preferably $(C_1-C_4)$-alkanediyl, and
$R^{13}$ and $R^{14}$ are identical or different and are hydrogen or $(C_1-C_4)$-alkyl;
$R^2$ is hydrogen, $(C_1-C_5)$-alkyl, $(C_6-C_{12})$-aryl-$(C_1-C_4)$-alkyl, $(C_4-C_6)$-cycloalkyl, $(C_4-C_6)$-cycloalkyl-$(C_1-C_2)$-alkyl, $(C_4-C_7)$-heteroaryl or *$C_4-C_7)$-heteroaryl-$(C_1-C_2)$-alkyl, it being possible for aryl and heteroaryl to be substituted as defined in claim 1, and where heteroaryl is defined as above for $R^6$ or $R^7$;
$R^3$ is isobutyl, benzyl or cyclohexylmethyl;
$R^4$ is hydrogen, $(C_1-C_5)$-alkyl, $(C_6-C_{10})$-aryl, $(C_6-C_{10})$-aryl-$(C_1-C_4)$-alkyl or hydroxyl;
$R^5$ is a radical of the formula II in which
$R^{15}$ ishydrogen, $(C_1-C_4)$-alkyl, $(C_1-C_4)$-alkoxy, $(C_1-C_4)$-alkylthio, $(C_1-C_4)$-alkylamino, hydroxyl, azido or halogen,
Het is as defined in claim 1, and
s is 0, 1 or 2; and B is a radical of an amino acid H—B—OH from the series phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 4-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylananine, 2-naphthylalanine, 4-nitrophenylalanine, norvaline, norleucine, cysteine, S-methylcysteine, N-methylhistidine, 1,2,3,4-tetrahydroisoquinoline-3-carboxylic acid, 2- and 4-thiazolyalanine, homophenylalanine, 2-amino-4-(2-thienyul)butyric acid, 2-amino-4-(3-thienyl)butyric acid, 3-(2-thienyl)serine, (Z)-dehydrophenylalanine, (E)-dehydrophenylalanine, 1,3-dioxolan-2-ylalanine, N-pyrrolylalanine and 1-, 3- or 4-pyrazolylalanine, especially compounds of the formula I in which $R^6$ and $R^7$ are hydrogen, $(C_1-C_4)$-alkyl, $(C_4-C_6)$-cycloalkyl, $(C_4-C_6)$-cycloalkyl-$((C_1-C_4)$-alkyl, $(C_6-C_{12})$-aryl which is optionally substituted by one or two identical or different radicals from the series methyl, ethyl, methoxy, ethoxy, halogen and amino, partially hydrogenated $(C_6-C_{12})$-aryl, $(C_6-C_{12})$-aryl-$(C_1-C_4)$-alkyl which is optionally substituted in the aryl moiety as described above for aryl, $(C_1-C_6)$-alkanoyl, $(C_6-C_{12})$-aryl-$(C_1-C_4)$-alkanoyl which is optionally substituted in the aryl moiety as described above for aryl, $(C_4-C_{10})$-heteroaryl-$(C_1-C_4)$-alkanoyl, $(C_1-C_4)$-alkoxy-$(C_1-C_4)$-alkanoyl, $(C_1-C_4)$-alkoxycarbonyl-$((C_1-C_6)$-alkanoyl, $(C_6-C_{12})$-aryloxycarbonyl-$(C_1-C_6)$-alkanoyl which is optionally substituted in the aryl moiety as described above for aryl, or $(C_6-C_{12})$-aryl-$(C_1-C_4)$-alkoxycarbonyl which is optionally substituted in the aryl moiety as described above for aryl, or $R^6$ and $R^7$ form, together with the nitrogen atom carrying them, a piperidino, pyrrolidino, morpholino, piperazino or thiomorpholino radical;

or $R^6$ is as defined above, and $R^7$ is amino, methylamino, ethylamino, di-$((C_1-C_2)$-alkylamino, hydroxyl, methoxy, ethoxy, methylfsulfonyl, ethylsulfonyl, phenylsulfonyl or carbamoyl;

$R^8$ has the meaning stated for $R^6$ and $R^7$;

$R^9$ is hydrogen, $(C_1-C_3)$-alkyl, $(C_4-C_6)$-cycloalkyl, $(C_4-C_6)$-cycloalkyl-$(C_1-C_2)$-alkyl, $(C_6-C_{12})$-aryl or $(C_6-C_{12})$-aryl-$(C_1-C_2)$-alkyl;

$R^{10}$, $R^{11}$ and $R^{12}$ are identical or different and are hydrogen or $(C_1-C_3)$-alkyl;

m is 0, 1 or 2;
n is 1, 2 or 3;
o is 0, 1 or 2;
p is 1, 2 or 3;
X is —CO— or —SO$_2$—;
Y is —(CH$_2$)$_q$—(CR$^{13}$R$^{14}$)$_r$— or —O—, in which
q is 0 or 1, 2,
r is 0, 1 or 2;

Z is —CH$_2$— and $R^{13}$ and $R^{14}$ are identical or different and are hydrogen or $(C_1-C_3)$-alkyl;

$R^2$ is $((C_1-C_4)$-alkyl, $(C_4-C_6)$-cycloalkyl, $(C_4-C_6)$-cycloalkyl-$(C_1-C_2)$-alkyl $C_6-C_{10})$-aryl-$(C_1-C_2)$-alkyl or $(C_4-C_6)$-heteroaryl$(C_1-C_2)$-alkyl, where aryl or heteroaryl is optionally substituted by one or two identical or different radicals from the series chlorine, fluorine, methoxy, hydroxyl and methyl;

$R^3$ is isobutyl, benzyl or cyclohexylmethyl;

$R^4$ is hydrogen or hydroxyl;

$R^5$ is a radical of the formula II in which $R^{15}$ is hydrogen or fluorine,

Het is a 2-, 3- or 4-pyridyl radical, a 2-, 4- or 5-imidazolyl radical or a 2-oxazolinyl radical, it being possible for the said heterocycles each to be substituted by one or two identical or different radicals from the series methyl, ethyl, propyl, allyl, fluorine, chlorine, bromine, CF$_3$ and methoxy, and s is 0, 1 or 2; and B is a radical of an amino acid H—B—OH from the series phenylalanine, histidine, tyrosine, tryptophan, methionine, leucine, isoleucine, asparagine, aspartic acid, β-2-thienylalanine, β-3-thienylalanine, β-2-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, 4-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norvaline, norleucine, 1,2,3,4-tetrahydroisoquinoline-3-carboxylic acid, 2- or 4-thiazolylalanine, homophenylalanine, 2-amino-4-(2-thienyl)butyric acid and 1-, 3- and 4-pyrazolylalanine; histidine or norvaline is preferred.

Very particularly preferred compounds of the formula I are those in which $R^6R^7$ and $R^8$ are identical or different and are hydrogen, $(C_1-C_4)$-alkyl, $(C_1-C_4)$-alkanoyl such as acetyl, $(C_6-C_{12})$-aryl-$(C_1-C_4)$-alkyl such as benzyl, $(C_7-C_{13})$-aroyl such as benzoyl, $(C_4-C_{10})$-heteroaroyl such as nicotinoyl, $(C_1-C_4)$-alkoxycarbonyl such as tert.-butoxycarbonyl, or benzyloxycarbonyl;

$R^9$ is as defined above, but is especially as defined in claim 3;

$R^{10}$, $R^{11}$ and $R^{12}$ are identical or different and are hydrogen, methyl or ethyl;

m is 0, 1 or 2;
n is 1, 2 or 3;
o is 0, 1 or 2;
p is 1, 2 or 3;
X is —CO— or —SO$_2$—;
Y is —(CH$_2$)$_q$—(CR$^{13}$R$^{14}$)$_r$— or —O— in which
q is 1,
r is 0;
Z is —CH$_2$— and
$R^{13}$ and $R^{14}$ are identical or different and are hydrogen, methyl or ethyl;
$R^2$ is cyclohexylmethyl, benzyl, 1- or 2-naphthylmethyl, 2-, 3- or 4-thienylmethyl, p-methoxybenzyl or p-fluorobenzyl, but especially benzyl; and
$R^3$, $R^4$, $R^5$ and B are as defined in claim 3.

The invention furthermore relates to a process for the preparation of compounds of the formula I, which comprises coupling a fragment with a terminal carboxyl group or a reactive derivative thereof to an appropriate fragment with a free amino group, where appropriate eliminating (a) protective group (s) temporarily introduced to protect other functional groups, and converting the compound obtained in this way, where appropriate, into the physiologically tolerated salt thereof.

Fragments of a compound of the formula I with a terminal carboxyl group have the following formula IVa or IVb,

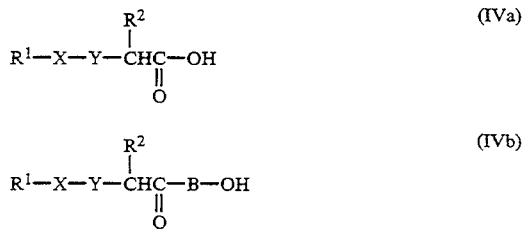

Fragments of a compound of the formula I with a terminal amino group have the following formula Va or Vb:

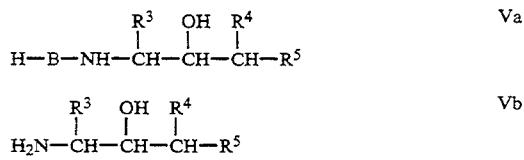

This entails linkage of the components only in the combination IVa with Va or IVb with Vb. Methods suitable for the production of an amide linkage are described, for example, in Houben-Weyl, Methoden der organischen Chemie [Methods of Organic Chemistry], Volume 15/2; Bodansky et al., Peptide synthesis, 2nd ed. (Wiley & Sons, New York 1976) or Gross, Meienhofer, The Peptides. Analysis, synthesis, biology (Academic Press, New York 1979). The following methods are preferably employed: Active ester method with N-hydroxysuccinimide or 1-hydroxybenzotriazole as ester component, coupling with a carbodiimide such as dicyclohexylcarbodiimide or with propanephosphonic anhydride or methylethylphosphinic anhydride and the mixed anhydride method with pivaloyl chloride (M. Zaoral, Coll. Chem. Commun., 1962, 27, 1273). The reaction is carried out in an inert solvent or solvent mixture at a temperature between −20° C. and the boiling point of the reaction mixture.

The preparation of the optically active amines of the formula Vb which are used as starting compounds and in which $R^2$, $R^3$ and $R^5$ are as defined above stats from optically active α-amino acids with retention of the center of asymmetry thereof. For this purpose, an N-protected amino aldehyde is prepared in a known manner and is coupled in an aldol-analogous addition onto an appropriate heteroarylalkyl building block and, after elimination of the N-protective group, yields amino alcohols of the formula Vb. When $R^4$=OH, an N-protected amino aldehyde is likewise used as starting material and is converted, for example, by aldol-analogous addition of unsaturated compounds, introduction of suitable protective groups and subsequent epoxidation into the required intermediates. Mixtures of diastereomers with respect to the OH-carrying center are obtained and are separated in a manner known per se, for example by fractional crystallization or by chromatography. The diastereomeric purity is checked by HPLC, and the enantiomeric purity can be checked in a known manner by conversion into Mosher derivatives (H. S. Mosher et al., J. Org. Chem. 34, 2543 (1969)).

N-protected amino aldehydes are prepared by the method of B. Castro et al. (Synthesis 1983, 676).

The aldol-analogous addition onto N-protected amino aldehydes (preferably N-tert.-butoxycarbonyl and benzyloxycarbonyl protective groups) is carried out in a solvent which is inert to bases, such as ether, THF, toluene, DMF, DMSO or dimethoxyethane.

Bases which can be used for the deprotonation of the heteroarylalkyl component are alkali metal alcoholates such as potassium O-tert.-butylate, sodium methylate, alkali metal hydrides such as sodium or potassium hydride, organometallic bases such as n-butyllithium, s-butyllithium, methyllithium or phenyllithium, sodamide and alkali metal salts of organic nitrogen bases, such as lithium diisopropylamide.

Carboxy-protected succinic acid derivatives are prepared in enantiomerically pure form by the method of J. J. Plattner et al. (J. Med. Chem 31, 2277 (1988)) and D. A. Evans et al. (J. Am. Chem. Soc. 104, 1737 (1982)).

Carbamoyl-substituted α-hydroxypropionic acid derivatives are prepared by reaction of enantiomerically pure or racemic α-hydroxypropionic acid derivatives and the N-containing ring systems substituted as defined with reactive carbonic acid derivatives such as, for example, phosgene, diphosgene, triphosgene, carbonyldiimidazole or di(1-benzotriazolyl) carbonate with the addition of suitable bases such as, for example, triethylamine, pyridine or ethyldiisopropylamine in an inert solvent.

Aminosulfonyl derivatives are prepared by condensation of the appropriately substituted amines with ω-chlorosulfonylalkylcarboxylic acid derivatives using bases and subsequently, after conventional elimination of temporarily introduced protective groups coupled by the process described above with fragments of the general formula I with a terminal amino group (such as, for example, Vb) using suitable activating methods. Inter alia, the chlorosulfonylpropionic acid derivatives are obtained, for example, by Michael addition of suitable sulfur-containing nucleophiles onto substituted acrylic acid derivatives with subsequent oxidation on the sulfur atom.

The preceding and subsequent operations necessary for the preparation of compounds of the formula I, such as the introduction and elimination of protective groups, are known from the literature and are described, for example, in T. W. Green, "Protective Groups in Organic Synthesis". Salts of compounds of the formula I with salt-forming groups are prepared in a manner known per se, for example by reacting a compound of the formula I with a basic group with a stoichiometric amount of a suitable acid.

Mixtures or stereoisomers, in particular mixtures of diastereomers, which are produced when racemic carboxylic acid derivatives and racemic amino acids H—B—OH are used, can be separated in a manner known per se by fractional crystallization or by chromatography.

The compounds of the formula I according to the invention have enzyme-inhibiting properties; in particular, they inhibit the action of the natural enzyme renin. Renin is a proteolytic enzyme which belongs to the class of aspartyl proteases and which is secreted as a consequence of various stimuli (volume depletion, sodium deficiency, β-receptor stimulation) from the juxtaglomerular cells of the kidney into the blood circulation. There it eliminates the decapeptide angiotensin I from the angiotensinogen secreted by the liver. Angiotensis I is converted by angiotensis converting enzyme (ACE) into angiotensis II. Angiotensis II plays an essential part of the regulation of blood pressure because it increases the blood pressure directly by vasoconstriction. In addition, it stimulates the secretion of aldosterone from the adrenal and in this way via inhibition of sodium excretion increases the extracellular fluid volume, which in turn contributes to an increase in blood pressure. Inhibitors of the enzymatic activity of renin bring about a reduced formation of angiotensis I, which is followed by a reduced formation of angiotensis II. The reduction of the concentration of this active peptide hormone is the direct cause of the lowering effect of renin inhibitors on blood pressure.

The activity of renin inhibitors can be examined by in vitro tests. This entails the reduction in the formation of angiotensis I being measured in various systems (human plasma, purified human renin).

1. Principal of the Assay

For example, human plasma which contains both renin and angiotensinogen is incubated at 37° C. with the compound to be tested. During this angiotensin I is liberated from angiotensinogen under the action of renin and can subsequently be measured with a commercially available radio-immunoassay. This angiotensis liberation is inhibited by renin inhibitors.

2. Obtaining Plasma

Human blood should be taken fresh (about 0.5 l per person; Bluko sampler from ASID Bonz und Sohn, UnterschleiBheim) and is collected in partially evacuated bottles by cooling in ice. Coagulation is prevented by addition of EDTA (final concentration 10 mM). After centrifugation (HS 4 rotor (Sorvall), 3,500 rpm, 0°-4° C., 15 min; repeat if necessary), the plasma is carefully removed by pipette and frozen in suitable portions at −30° C. Only plasmas with sufficiently high renin activity are used for the assay. Plasmas with low renin activity are activated as (prorenin→renin) by a low-temperature treatment (−4° C., 3 days).

3. Assay Procedure

Antiotensin I is determined using the Renin-Maia ® kit (Serono Diagnostics S. A., Coinsins, Switzerland). The plasma is incubated as instructed therein:
Incubation mixture:
1000 μl of plasma (thawed at 0°-4° C.)
100 μl of phosphate buffer (pH 7.4) addition of $10^{-4}$M ramiprilat
10 μl of PMSF solution
10 μl of 0.1% Genapol PFIC
12 μl of DMSO or test product In general, $10^{-2}$M solutions of the test products are prepared in 100% dimethyl sulfoxide (DMSO) and diluted appropriately with DMSO; the incubation mixture contains not more than 1% DMSO.

The mixtures are mixed in ice and, for the incubation, placed in a waterbath at 37° C. for 1 hour. A total of 6 samples (100 μl each) are taken, without further incubation, from an additional mixture without inhibitor for determination of the initial angiotensin I content of the plasma used.

The concentrations of the test products are selected so that the range of 10–90% enzyme inhibition is approximately covered (at least five concentrations). At the end of the incubation time, three 100 μl samples from each mixture are frozen in precooled Eppendorf tubes on dry ice and stored at about −25° C. for the antiogensin I determination (means from three separate samples).

Angiotensin I Radioimmunoassay (RIA)

The instructions for use of the RIA kit (Renin Maia ® kit, Serono Diagnostics S. A., Coinsins, Switzerland) are followed exactly.

The calibration plot covers the range from 0.2 to 25.0 ng of angiotensin I per ml. The baseline angiotensin I content of the plasma is subtracted from all the measurements. The plasma renin activity (PRA) is reported as ng of ang I/ml/33 hour. PRA levels in the presence of the test substances are related to a mixture without inhibitor(=100%) and reported as % remaining activity. The $IC_{50}$ is read off from a plot of % remaining activity against the concentration (M) of the test product (logarithmic scale).

The compounds of the general formula I described in the present invention show inhibitory actions at concentrations of about $10^{-5}$ to $10^{-10}$ mol/l in the in vitro assay.

Renin inhibitors lower the blood pressure of salt-depleted animals. Because human renin differs from the renin of other species, primates (marmosets, Rhesus monkeys) are used for the in vivo assay of renin inhibitors. There is substantial homology in the sequence of primate renin and human renin. Endogenous renin secretion is stimulated by i.v. injection of furosemide. The test compounds are then administered, and their effect on blood pressure and heart rate is measured. The compounds of the present invention are active in this test in a dose range of about 0.1–5 mg/kg i.v. and in the dose range of about 1–50 mg/kg on intraduodenal administration by gastroscope. The compounds of the general formula I described in the present invention can be used as antihypertensives and for the treatment of cardiac insufficiency.

HIV protease is cut autocatalytically out of the GAG-POL polypeptide and subsequently cleaves the precursor peptide p55 into the core antigens p17, p24 and p14. It is thus an essential enzyme, and inhibition thereof interrupts the life cycle of the virus and suppresses its multiplication.

Biological tests have shown that the compounds of the invention have an enzyme-inhibitory action and inhibit viral enzymes such as HIV protease too. The inhibiting action on HIV protease has particular importance and qualifies the compounds according to the invention in particular for the therapy and prophylaxis of disorders caused by infection with HIV. The compounds of the general formula I according to the invention have inhibiting actions at concentrations of $10^{-4}$ to $10^{-9}$ mol/l inhibiting actions at concentrations of $10^{-4}$ to $10^{-9}$ mol/l in the in vitro tests used.

The invention also relates to the use of compounds of the formula I for the preparation of pharmaceuticals for the therapy of high blood pressure and the treatment of congestive heart failure and for the therapy and prophylaxis of viral disorders, in particular of disorders caused by HIV, as well as the said pharmaceuticals.

Pharmaceutical products contain an effective amount of the active compound of the formula I together with an inorganic or organic pharmaceutically utilizable excipient. Intranasal, intravenous, subcutaneous or oral use is possible. The dosage of the active compound depends on the warm-blooded species, the body weight, age and on the mode of administration.

The pharmaceutical products of the present invention are prepared in dissolving, mixing, granulating and coating processes known per se.

For a form for oral use, the active compounds are mixed with the additives customary for this purpose, such as excipients, stabilizers or inert diluents, and converted by customary methods into suitable dosage forms such as tablets, coated tablets, hard gelatine capsules, aqueous, alcoholic or oily suspensions or aqueous, alcoholic or oily solutions. Examples of inert vehicles which can be used are gum arabic, magnesia, magnesium carbonate, potassium phosphate, lactose, glucose, magnesium stearyl fumarate or starch, especially corn starch. This preparation can be both as dry and wet granules. Examples of suitable oily excipients or solvents are vegetable or animal oils, such as sunflower oil and fish liver oil.

For subcutaneous or intravenous administration, the active compounds or the physiologically tolerated salts thereof are converted into solutions, suspensions or emulsions, if desired with the substances customary for this purpose, such as solubilizers, emulsifiers or other auxiliaries. Examples of suitable solvents are: water, physiological saline solutions or alcohols, for example ethanol, propanediol or glycerol, as well as sugar solutions such as glucose or mannitol solutions, or else a mixture of the various solvents mentioned.

| List of abbreviations used: | |
| --- | --- |
| Boc | tert.-butyloxycarbonyl |
| BuLi | n-butyllithium |
| DCC | dicyclohexylcarbodiimide |
| DCI | desorption chemical ionization |
| DNP | 2,4-dinitrophenyl |
| DME | dimethoxyethane |
| DMF | dimethylformamide |
| EA | ethyl acetate |
| FAB | fast atom bombardment |
| Fmoc | fluorenylmethoxycarbonyl |
| h | hour |
| HOBt | 1-hydroxybenzotriazole |
| M | molecular peak |
| MS | mass spectrum |
| min | minutes |
| NEM | N-ethylmorpholine |
| THF | tetrahydrofuran |
| Trt | triphenylmethyl |

The examples which follow are intended to illustrate the preparation of the compounds according to the invention without restricting the invention to these.

EXAMPLE 1

N-[N-(2(R)-Benzyl-3-(4-(tert.-butyloxycarbonyl)amino-1-piperidinyl-carbonyl)-propionyl)-L-histidinyl]-(2S,3R,4S)-1-cyclohexyl-3,4-dihydroxy-6-(2-pyridyl)-2-hexylamide 0.12 g of the compound for Example 1a is stirred with 60 mg of thiophenol in 4 ml of abs. acetonitrile at room temperature for 2 hours. Concentration and codistillation with toluene twice are followed by chromatography on silica gel with $CH_2Cl_2$/MeOH/sat. $NH_3$ (10:1:0.1). 72 mg of the title compound are obtained as a yellow amorphous solid.

$R_f$(SiO$_2$, $CH_2Cl_2$/MeOH/sat. $NH_3$ 10:1:0.1):0.33
MS (FAB):801 (M+H)

a)
N-[N-(2(R)-Benzyl-3-(4-(tert.-butyloxycarbonyl)amino-1-piperidinyl-carbonyl)-propionyl)-L-histininyl(DNP)]-(2S,3R,4S)-1-cyclohexyl-3,4-dihydroxy-6-(2-pyridyl)-2-hexylamide 0.4 g of BOC-L-His(DNP)-(2S,3R,4S)-1-cyclohexyl-3,4-dihydroxy-6-(2-pyridyl)-2-hexylamide (compound from Example 1f) is stirred with 6 ml of trifluoroacetic acid in 6 ml of abs. $CH_2Cl_2$ at room temperature for 2 hours. The residue resulting from concentration is taken up in 1M $NaHCO_3$ solution, the mixture is extracted three times with EA, and the EA phase is dried over $Na_2SO_4$. The residue after concentration is dissolved in 6 ml of abs. DMF, 224.5 mg of the compound from Example 1b, 118.6 mg of N,N'-dicyclohexylcarbodiimide and 89.3 mg of 1-hydroxybenzotriazole are added, and the solution is adjusted to pH 9 with N-ethylmorpholine and left to stand for 48 hours. Filtration is followed by dilution with EA and washing once each with saturated $NaHCO_3$ solution, water and saturated brine, drying over $Na_2SO_4$ and concentration. Chromatography on silica gel ($CH_2Cl_2$/MeOH 20:1) yields 140 mg of the title compound as a yellow resin.

$R_f$(SiO$_2$, $CH_2Cl_2$/MeOH 10:1):0.42
MS (FAB):968 (M+H), 974 (M+Li).

b)
2(R)-Benzyl-3-[4-(tert.-butyloxycarbonyl)amino-1-piperidinyl-carbonyl]-propionic acid 1.3 g of the compound from Example 1c are dissolved in 60 ml of abs. ethanol and hydrogenated (1.1 bar $H_2$) with 200 mg of Pd/C (10% Pd) at room temperature for 1 hour. After filtration and removal of the solvent in vacuo, 0.74 g of the title compound crystallizes from cold diethyl ether.

$R_f$(SiO$_2$,
Melting point: 135°–136° C.
MS (DCI):391 (M+H)

c) Benzyl 2(R)-benzyl-3-[4-(tert.-butyloxycarbonyl)amino-1-piperidinyl-carbonyl]-propionate 1.0 g of benzyl (2R)-2-(carboxymethyl)-3-phenyl-propionate (prepared as in J. Med. Chem. 31 (198) 2277) is stirred with 0.31 ml of oxalyl chloride and 0.5 ml of abs. DMF in 50 ml of abs. $CH_2Cl_2$ at 0° C. for 1 hour. The residue after concentration is taken up in 25 ml of abs. $CH_2Cl_2$, the solution is adjusted to pH 7 with triethylamine, and 0.71 g of the compound from Example 1d and 0.47 ml of triethylamine dissolved in 50 ml of abs. $CH_2Cl_2$ are added dropwise. The mixture is stirred at 0° C. for 3 hours and then concentrated, the residue is taken up in EA, washed once each with cold 2N HCl and saturated $NaHCO_3$ solution and dried over $MgSO_4$. Removal of the solvent in vacuo yielded 1.35 g of the title compound as a pale yellow oil.

$R_f$(SiO$_2$, $CH_2Cl_2$/MeOH 9:1):0.5
MS (DCI):481 (M+H)

d) 4-(tert.-Butyloxycarbonyl)amino-piperidine 10.0 g of the compound from Example 1e are hydrogenated (1.1 bar $H_2$) in 60 ml of ethanol/glacial acetic acid 9:1 with 1.0 g of Pd/C (10% Pd) at room temperature for 1 hour. Filtration, concentration, codistillation with toluene twice, taking up in EA, extraction by shaking with sat. NaHCO$_3$ solution and saturated brine, drying over MgSO$_4$ and concentration result in a beige residue from which 5.5 g of the title compound are obtained in the form of white crystals by recrystallization from EA.

R$_f$(SiO$_2$, CH$_2$Cl$_2$/MeOH 9:1):0.11
Melting point: 159°–161° C.
MS (DCI):201 (M+H)

e)

1-Benzyl-4-[(tert.-butyloxycarbonyl)amino]-piperidine 10.0 g of 4-amino-N-benzylpiperidine are dissolved in 100 ml of abs. CH$_2$Cl$_2$, 11.5 g of di-tert.-butyl dicarbonate are added, and the solution is stirred at room temperature for 2 hours and left to stand for 12 hours. Concentration and recrystallization of the residue from EA provide 12.9 g of the title compound as white crystals.

R$_f$(SiO$_2$, CH$_2$Cl$_2$/MeOH 8:2):0.23
Melting point: 123° C.
MS (DCI):291 (M+H)

f) BOC-L-His(DNP) (2S,3R,4S)-1-cyclohexyl-3,4-dihydroxy-6-(2-pyridiyl)-2-hexylamide 0.5 mmol of the (2S,3R,4S) isomer from Example 1g is stirred with 5 ml of HCl in DME (saturated) for 2 hours. The residue after concentration is dissolved in 3 ml of abs. DMF. 0.5 mmol each of BOC-His(DNP)-OH, N,N'-dicyclohexylcarbodiimide and 1-hydroxybenzotriazole are added. The solution is adjusted to pH 9 with N-ethylmorpholine and stirred for 24 hours. Filtration is followed by dilution with EA, washing once each with saturated NaHCO$_3$ solution, water and saturated brine, drying over MgSO$_4$ and concentration. Chromatography on silica gel (CH$_2$Cl$_2$/MeOH 20:1) provides the title compound as a yellow resin.

MS (FAB):696 (M+H)

g)

(2S,3R,4S)-2-(tert.-Butyloxycarbonyl)amino-1-cyclohexyl-3,4-dihydroxy-6-(2-pyridyl)-hexane 1.4 ml of n-butyllithium are added to 93.0 mg of 2-picoline in 10 ml of THF at −78° C. Warming to room temperature is followed by stirring for 30 minutes and then cooling to −40° C. 1 mmol of (2RS,3R,4S)-3-tert.-butyldimethyl-silyloxy-4-(tert.butyloxycarbonylamino)-5-cyclohexyl-1,2-oxopentane (disclosed in EP-A 189,203, Example 6) is added (dissolved in 5 ml of THF). Stirring at room temperature for 10 hours is followed by dilution with water and extraction with methyl tert.-butyl ether. The crude product after concentration is dissolved in THF and stirred with 5 ml of a 1M solution of tetrabutylammonium fluoride in THF at 0° C. for 1 hour. Dilution with water, extraction with EA and concentration result in 0.15 g of the (2S,3R,4S) isomer (MS (FAB):391 (M+H)) and 0.12 g of the (2S,3S,4S) isomer (MS (FAB):391 (M+H)).

EXAMPLE 2

N-[N-(3-(4-Amino-1-piperidinyl-carbonyl)-2(R)-benzylpropionyl)-L-histidinyl]-(2S,3R,4S)-1-cyclohexyl-3,4-di-hydroxy-6-(2-pyridyl)-2-hexylamide acetate 70.0 mg of the compound from Example 1 are stirred with 4 ml of trifluoroacetic acid in 4 ml of abs. CH$_2$Cl$_2$ at room temperature for 2 hours. Concentration is followed by taking up twice in toluene and concentrating each time. The residue is dissolved in a little water, the pH of the solution is adjusted to 5 by addition of Amberlite ion exchanger (acetate form), the ion exchanger is filtered off, and the filtrate is freeze-dried. The result is 63.8 mg of the title compound in the form of a pale yellow amorphous solid.

MS (FAB):702 (M+H)

EXAMPLE 3

N-[N-(2(S)-(4-(tert.-Butyloxycarbonyl)amino-1-piperidinylcarbonyloxy)-3-phenyl-propionyl)-L-histidinyl]-(2S,3R,4S)-1-cyclohexyl-3,4-dihydroxy-6-(2-pyridyl)-2-hexylamide This compound is prepared from the compound from Example 3a by the process stated in Example 1; yellow amorphous solid.

MS (FAB):804 (M+H)

a)

N-[N-(2(S)-(4-(tert.-Butyloxycarbonyl)amino-1-piperidinylcarbonyloxy)-3-phenyl-propionyl)-L-histidinyl-(DNP)]-(2S,3R,4S)-1-cyclohexyl-3,4-dihydroxy-6-(2-pyridyl)-2-hexylamide This compound is prepared from the compounds from Examples 1f and 3b by the process detailed in Example 1a; yellow resin.

R$_f$(SiO$_2$, CH$_2$Cl$_2$/MeOH 10:1):0.35
MS (FAB):970 (M+H);

b)

2(S)-[4-(tert.-Butyloxycarbonyl)amino-1-piperidinylcarbonyloxy]-3-phenyl-propionic acid 465.0 mg of the compound from Example 3c are stirred with 5 ml of 1N sodium hydroxide solution in 5 ml of methanol at 0° C. for 3 hours. After concentration and after the residue has been taken up in water, the solution is adjusted to pH 5 with 2N hydrochloric acid and extracted with EA several times. The organic phase is washed with saturated brine, dried over MgSO$_4$ and concentrated. Recrystallization of the residue from EA/n-heptane yields 242.0 mg of the title compound.

R$_f$(SiO$_2$, CH$_2$Cl$_2$/MeOH 9:1):0.29
Melting point: 100°–103° C.
MS (DCI):293 (M−BOC+2H), 201 (M−C$_{10}$H$_9$O$_4$+2H)

c) Ethyl 2(S)-[4-(tert.-butyloxycarbonyl)amino-1-piperidinylcarbonyloxy]-3-phenyl-propionate 1.1 g of di(1-benzotriazolyl) carbonate (70% pure) and 332.7 mg of ethyldiisopropylamine are added to 500.0 mg of ethyl 2(S)-hydroxy-3-phenyl-propionate (prepared from L-3-puenyllactic acid and ethanolic HCl solution) in 10 ml of absolute CH$_2$Cl$_2$. The resulting solution is first stirred at room temperature for 7 hours and then left to stand for 12 hours. Addition of 512.5 mg of the compound from Example 1d and 332.7 mg of ethyldiisopropylamine is followed by stirring at room temperature for a further 7 hours. The reaction solution is diluted with 30 ml of EA, washed with saturated Na$_2$CO$_3$ solution and saturated brine and dried over Na$_2$SO$_4$. Concentration and chromatography on silica gel (n-heptane/EA 2:1) result in 480.0 mg of the title compound as a colorless oil.

R$_f$(SiO$_2$, n-heptane/EA 2:1):0.20
MS (DCI):421 (M+H), 321 (M−BOC+H)

EXAMPLE 4

N-[N-(2(S)-(4-Amino-1-piperidinyl-carbonyloxy)-3-phenyl-propionyl)-L-histinidinyl]-(2S,3R,4S)-1-cyclohexyl-3,4-dihydroxy-6-(2-pyridinyl)-2-hexylamide acetate This compound is prepared from the compound from Example 3 by the process detailed in Example 2; beige amorphous solid.
MS (FAB):704 (M+H)

EXAMPLE 5

N-[N-(2(R)-Benzyl-3-(N-benzyl-piperidinyl-4-aminocarbonyl)propionyl)-L-histinidinyl]-(2S,3R,4S)-1-cyclohexyl-3,4-dihydroxy-6-(2-pyridyl)-2-hexylamide This compound is prepared from the compound from Example 5a by the process stated in Example 1; yellow resin.
MS (FAB):792 (M+H)

a)
N-[N-(2(R)-Benzyl-3-(N-benzyl-piperidinyl-4-aminocarbonyl)propionyl)-L-histidinyl(DNP)]-(2S,3R,4S)-1-cyclohexyl-3,4-dihydroxy-6-(2-pyridyl)-2-hexylamide This compound is prepared from the compounds from Examples 1g and 5b by the process stated in Example 1a.
MS (FAB):958 (M+H), 964 (M+Li)

b)
2(R)-Benzyl-3(N-benzyl-piperidinyl-4-aminocarbonyl)-propionic acid 345.0 mg of the compound from Example 5c are hydrogenated (1.1 bar $H_2$) in 30 ml of ethanol with 70 mg of Pd/C (10% Pd) at room temperature for 10 minutes. Filtration and concentration yield 269.0 mg of the title compound in the form of a pale brown oil.
$R_f$(SiO$_2$, CH$_2$Cl$_2$/MeOH 1:1):0.21
MS (DCI): 381 (M+H)

c) Benzyl 2(R)-benzyl-3-(N-benzyl-piperidinyl-4-aminocarbonyl)-propionate

This compound is prepared from 4-amino-N-benzyl-piperidine by the process which is described in Example 1c and which is modified here by use of 2 equivalents of base, omission of the extraction with 2N HCl solution, and working up by chromatography on silica gel (CH$_2$Cl$_2$/EA 7:3).
$R_f$(SiO$_2$, CH$_2$Cl$_2$/EA 7:3):0.25
MS (DCI):471 (M+H)

EXAMPLE 6

N-[N-(2(R)-Benzyl-3-(piperidinyl-4-aminocarbonyl)-propionyl)-L-histidinyl]-(2S,3R,4S)-1-cyclohexyl-3,4-dihydroxy-6-(2-pyridinyl)-2-hexylamide acetate 40.0 mg of the compound from Example 5 are hydrogenated (1.1 bar $H_2$) in 10 ml of ethanol/glacial acetic acid 9:1 with 10 mg of Pd/C (10% Pd) at room temperature for 1 hour. Filtration, concentration and codistillation twice with toluene are followed by the residue being taken up in water and the solution freeze-dried. The result is 22.3 mg of the title compound as a beige amorphous solid.
MS (FAB):702 (M+H)

EXAMPLE 7

N-[N-(2(S)-(N-Benzyl-piperidinyl-4-aminocarbonyloxy)-3-phenyl-propionyl-L-histidinyl]-(2S,3R,4S)-1-cyclohexyl-3,4-dihydroxy-6-(2-pyridyl)-2-hexylamide This compound is prepared from the compound from Example 7a by the process stated in Example 1; yellow amorphous solid
MS (FAB):794 (M+H)

a)
N-[N-(2(S)-(N-Benzyl-piperidinyl-4-aminocarbonyloxy)-3-phenyl-propionyl)-L-histidinyl(DNP)]-(2S,3R,4S)-1-cyclohexyl-3,4-dihydroxy-6-(2-pyridyl)-2-hexylamide This compound results from the compounds from Examples 1g and 7b by the process stated in Example 1a; yellow resin.
MS (FAB):960 (M+H); 966 (M+Li)

b)
2(S)-(N-Benzyl-piperidinyl-4-aminocarbonyloxy)-3-phenyl-propionic acid 400.0 mg of the compound from Example 7c are stirred with 1 ml of 1N sodium hydroxide solution in 5 ml of ethanol at 0° C. for 3 hours and left to stand at about 8° C. for 12 hours. The residue after concentration is dissolved in water, neutralized with 2N hydrochloric acid and, after addition of sodium chloride, extracted several times with EA. Drying over Na$_2$SO$_4$, concentration and chromatography on silica gel (CH$_2$Cl$_2$/MeOH 2:1) provide 224.0 mg of the title compound.
MS (DCI): 383 (M+H)

c) Ethyl 2(S)-(N-benzyl-piperidinyl-4-aminocarbonyloxy)-3-phenyl-propionate

This compound is prepared from 4-amino-N-benzyl-piperidine by the process detailed in Example 3c, using in this case pyridine as auxiliary base and n-heptane/EA 1:1 as mobile phase in the working up by chromatography; white crystals.
$R_f$(SiO$_2$, n-heptane/EA 1:1):0.25
Melting point: 72°–74° C.
MS (DCI):411 (M+H)

EXAMPLE 8

N-[N-(3-Phenyl-2(S)-(piperidinyl-4-aminocarbonyloxy)-propionyl)-L-histidinyl]-(2S,3R,4S)-1-cyclohexyl-3,4-dihydroxy-6-(2-pyridinyl)-2-hexylamide acetate This compound is prepared from the compound from Example 7 by the process detailed in Example 6; pale brown amorphous solid.
MS (FAB):702 (M+H)

EXAMPLE 9

N-[N-(2(R)-Benzyl-3-(4-(tert.-butyloxycarbonyl)amino-1-piperidinyl-carbonyl)-propionyl)-L-histidinyl]-(2S,3S)-1-cyclohexyl-3-hydroxy-6-(2-pyridyl)-2-hexylamide 80 mg of the compound from Example 9a are stirred in 1 ml of 90% strength acetic acid at 60° C. for 3 hours. The residue after concentration is taken up in EA, washed twice with saturated NaHCO$_3$ solution and brine and dried over Na$_2$SO$_4$. Concentration and chromatography on silica gel (CH$_2$Cl$_2$/MeOH 9:1) provide 31.2 mg of the title compound.
MS (FAB):786 (M+H)

a)
N-[N-(2(R)-Benzyl-3-(4-(4-(tert.-butyloxycarbonyl)-amino-1-piperidinyl-carbonyl)-propionyl)-L-histidinyl(Trt)]-(2S,3S)-1-cyclohexyl-3-hydroxy-6-(2-pyridyl)-2-hexylamide 375 mg of the compound from Example 9b are dissolved in 4 ml of abs. DMF, 225 mg of the compound from Example 1g, 120 mg of N,N'-dicyclohexylcarbodiimide and 90 mg of 1-hydroxybenzotriazole are added, and the solution is adjusted to pH 9 with N-ethylmorpholine. The mixture is left to stand at room temperature for 48 hours and then filtered, and the filtrate is diluted with EA and washed once each with saturated NaHCO$_3$ solution, water and saturated brine. Drying, concentration and chromatography on silica gel yield 298 mg of the title compound.
MS (FAB):1028 (M+H)

b) H-His(Trt)
(2S,3S)-1-cyclohexyl-3-hydroxy-6-(2-pyridyl)-2-hexylamide 600 mg of the compound described in Example 9c are stirred with 0.65 ml of diethylamine in 5 ml of abs. DMF at room temperature for 1 hour. Concentration and chromatography on silica gel (CH$_2$Cl$_2$/MeOH 9:1) provide 380 mg of the title compound.
MS (FAB):656 (M+H c)
Fmoc-His(Trt)-(2S,3S)-1-cyclohexyl-3-hydroxy-6-(2-pyridyl)-2-hexylamide 1.0 g of Fmoc-His(Trt)-OH, 283 mg of 1-hydroxybenzotriazole, 370 mg of N,N'-dicyclohexylcarbodiimide and 0.25 ml of N-ethylmorpholine are dissolved in 10 ml of abs. DMF and stirred at room temperature for 1 hour. A solution of 483 mg of 2(S)-amino-1-cyclohexyl-3(S)-hydroxy-6-(2-pyridyl)hexane (disclosed in EP-A 0,255,082) in 4 ml of DMF is added dropwise to this mixture, which is then stirred at room temperature for 12 hours. Addition of 5 ml of water is followed by filtration to remove the urea which has formed and by taking up in EA. The organic phase is washed repeatedly with saturated NaHCO$_3$ solution and saturated brine, dried over MgSO$_4$ and, after filtration, concentrated in vacuo. Chromatography on silica gel provides 880 mg of the said compound.
Melting point: 85° C.
MS (FAB):878

EXAMPLE 10
N-[N-(3-(4-Amino-1-piperidinyl-carbonyl)-2(R)-benzylpropionyl)-L-histidinyl]-(2S,3S)-1-cyclohexyl-3-hydroxy-6-(2-pyridyl)-2-hexylamide acetate 25 mg of the compound from Example 9 are stirred with 2 ml of trifluoroacetic acid in 2 ml of abs. CH$_2$Cl$_2$ at room temperature for 2 hours. The residue after concentration and codistillation twice with toluene is dissolved in water, the solution is adjusted to pH 5 by addition of Amberlite ion exchanger (acetate form) and is filtered, and the filtrate is lyophilized. The title compound is obtained in a yield of 20 mg.
MS (FAB):686 (M+H)

EXAMPLE 11
N-[N-(2(S)-(4-(tert.-Butyloxycarbonyl)amino-1-piperidinyl-carbonyloxy)-3-phenyl-propionyl)-L-histidinyl]-(2S,3S)-1-cyclohexyl-3-hydroxy-6-(2-pyridyl)-2-hexylamide This compound is prepared from the compound from Example 11a by the process stated in Example 9.
MS (FAB):788 (M+H)

a)
N-[N-(2(S)-(4-(tert.-Butyloxycarbonyl)amino-1-piperidinyl-carbonyloxy)-3-phenyl-propionyl)-L-histidinyl(Trt)]-(2S,3S)-1-cyclohexyl-3-hydroxy-6-(2-pyridyl)-2-hexylamide This compound is prepared from the compounds from Examples 3b and 9b by the process stated in Example 9a.
MS (FAB):1030 (M+H)

EXAMPLE 12
N-[N-(2(S)-(4-Amino-1-piperidinyl-carbonyloxy)-3-phenylpropionyl)-L-histidinyl]-(2S,3S)-1-cyclohexyl-3-hydroxy-6-(2-pyridyl)-2-hexylamide acetate The title compound is prepared by the process described in Example 2 from the compound described in Example 11.
MS (FAB):688 (M+H)

EXAMPLE 13
N-[N-(2(R)-Benzyl-3-(N-benzyl-piperidinyl-4-aminocarbonyl)-propionyl)-L-histidinyl]-(2S,3S)-1-cyclohexyl-3-hydroxy-6-(2-pyridyl)-2-hexylamide The title compound is prepared by the process described in Example 9 from the compound detailed in Example 13a.
MS (FAB):776 (M+H)

a)
N-[N-(2(R)-Benzyl-3-(N-benzyl-piperidinyl-4-aminocarbonyl)propionyl)-L-histidinyl(Trt)]-(2S,3S)-1-cyclohexyl-3-hydroxy-6-(2-pyridyl)-2-hexylamide This compound is prepared from the compounds from Examples 5b and 9b by the process described in Example 9a.
MS (FAB):1018 (M+H)

EXAMPLE 14
N-[N-(2(R)-Benzyl-3-(piperidinyl-4-aminocarbonyl)-propionyl)-L-histidinyl]-(2S,3S)-1-cyclohexyl-3-hydroxy-6-(2-pyridyl)-2-hexylamide acetate The title compound is prepared from the compound from Example 13 by the process stated in Example 6.
MS (FAB):686 (M+H)

EXAMPLE 15
N-[N-(2(S)-(N-Benzyl-piperidinyl-4-aminocarbonyloxy)-3-phenyl-propionyl)-L-histidinyl]-(2S,3S)-1-cyclohexyl-3-hydroxy-6-(2-pyridyl)-2-hexylamide The title compound is prepared from the compound stated in Example 15a by the process described in Example 9.
MS (FAB):778 (M+H)

a)
N-[N-(2(S)-(N-Benzyl-piperidinyl-4-aminocarbonyloxy)-3-phenyl-propionyl)-L-histidinyl(Trt)]-(2S,3S)-1-cyclohexyl-3-hydroxy-6-(2-pyridyl)-2-benzylamide The title compound is prepared from the compounds detailed in Examples 7b and 9b by the process described in Example 9a.
MS (FAB):1020 (M+H)

EXAMPLE 16

N-[N-(3-Phenyl-2(S)-(piperidinyl-4-aminocarbonyloxy)-propionyl)-L-histidinyl]-(2S,3S)-1-cyclohexyl-3-hydroxy-6-(2-pyridyl)-2-hexylamide acetate The title compound is prepared from the compound from Example 15 by the process described in Example 6.
MS (FAB):688 (M+H)

EXAMPLE 17

N-[N-(2(R)-Benzyl-3-(4-(tert.-butyloxycarbonyl)amino-1-piperidinyl-carbonyl)-propionyl)-L-norvalinyl]-(2S,3R,4S)-1-cyclohexyl-3,4-dihydroxy-6-(2-pyridyl)-2-hexylamide The title compound is prepared from the compounds from Examples 1b and 17a by the process stated in Example 1a.

a)
BOC-Nva-(2S,3R,4S)-1-cyclohexyl-3,4-dihydroxy-6-(2-pyridyl)-2-hexylamide

The title compound is prepared from BOC-norvaline and the compound from Example 1g by the process stated in Example 1a.
MS (FAB): 492 (M+H)

EXAMPLE 18

N-[N-(3-(4-Amino-1-piperidinyl-carbonyl)-2(R)-benzylpropionyl)-L-norvalinyl]-(2S,3R,4S)-1-cyclohexyl-3,4-dihydroxy-6-(2-pyridyl)-2-hexylamide acetate The title compound is prepared from the compound from Example 17 by the process stated in Example 2.
MS (FAB):664 (M+H)

EXAMPLE 19

N-[N-(2(S)-(4-(tert.-Butyloxycarbonyl)amino-1-piperidinyl-carbonyloxy)-3-phenyl-propionyl)-L-noravlinyl]-(2S,3R,4S)-1-cyclohexyl-3,4-dihydroxy-6-(2-pyridyl)-2 -hexylamide The title compound is prepared from the compounds from Examples 3b and 17a by the process stated in Example 1a.
MS (FAB):766 (M+H)

EXAMPLE 20

N-[N-(2(S)-(4-Amino-1-piperidinyl-carbonyloxy)-3-phenyl-propionyl)-L-norvalinyl]-(2S,3R,4S)-1-cyclohexyl-3,4-dihydroxy-6-(2-pyridyl)-2-hexylamide acetate The title compound is prepared from the compound from Example 19 by the process stated in Example 2.
MS (FAB):666 (M+H)

EXAMPLE 21

N-[N-(2(R)-Benzyl-3-(N-benzyl-piperidinyl-4-aminocarbonyl)propionyl)-L-norvalinyl]-(2S,3R,4S)-1-cyclohexyl-3,4-dihydroxy-6-(2-pyridyl)-2-hexylamide The title compound is prepared from the compounds from Examples 5b and 17a by the process stated in Example 1a.
MS (FAB):754 (M+H)

EXAMPLE 22

N[N-(2(R)-Benzyl-3-(piperidinyl-4-aminocarbonyl)propionyl)-L-norvalinyl]-(2S,3R,4S)-1-cyclohexyl-3,4-dihydroxy-6-(2-pyridyl)-2-hexylamide acetate The title compound is prepared from the compound from Example 21 by the process described in Example 6.
MS (FAB):664 (M+H)

EXAMPLE 23

N-[N-(2(S)-(N-Benzyl-piperidinyl-4-aminocarbonyloxy)-3-phenyl-propionyl)-L-norvalinyl]-(2S,3R,4S)-1-cyclohexyl-3,4-dihydroxy-6-(2-pyridyl)-2-hexylamide The title compound is prepared from the compounds from Examples 7b and 17a by the process described in Example 1a.
MS (FAB):756 (M+H)

EXAMPLE 24

N-[N-(3-Phenyl-2(S)-(piperidinyl-4-aminocarbonyloxy)propionyl)-L-norvalinyl]-(2S,3R,4S)-1-cyclohexyl-3,4-dihydroxy-6-(2-pyridyl)-2-hexylamide acetate The title compound is prepared from the compound from Example 23 by the process stated in Example 6.

EXAMPLE 25

N-[N-(3-(4-(tert.-Butyloxycarbonyl)amino-1-piperidinylcarbonyl)-2(R)-(1-naphthylmethyl)propionyl)-L-histidinyl]-(2S,3R,4S)-1-cyclohexyl-3,4-dihydroxy-6-(2-pyridyl)-2-hexylamide The title compound is prepared from the compound from Examples 25a by the process stated in Example 1.
MS (FAB):852 (M+H)

a)
N-[N-(3-(4-(tert.-Butyloxycarbonyl)amino-1-piperidinyl-carbonyl)-2(R)-(1-naphthylmethyl)propionyl)-L-histidinyl(DNP)]-(2S,3R,4S)-1-cyclohexyl-3,4-dihydroxy-6-(2-pyridyl)-2-hexylamide The title compound is prepared from the compounds from Examples 1f and 25b by the process stated in Example 1a.
MS (FAB):1018 (M+H)

b)
3-[4-(tert.-Butyloxycarbonyl)amino-1-piperidinylcarbonyl]-2(R)-(1-naphthylmethyl)-propionic acid The title compound is prepared from the compound from Examples 25c by the process stated in Example 1b.
MS (DCI):441 (M+H)

c) Benzyl 3-[4-(tert.-butyloxycarbonyl)amino-1-piperidinyl]-2(R)-(1-naphthylmethyl)-propionate The title compound is prepared from benzyl 2(R)-(carboxymethyl)-3-(1-naphthyl)-propionate (prepared as in J. Med. Chem. 31 (1988) 2277–2288) and the compound from Example 1d by the process stated in Example 1c.

MS (DCI):531 (M+H)

EXAMPLE 26

N-[N-(3-(4-Amino-1-piperidinyl-carbonyl)-2(R)-(1-naphthylmethyl)propionyl)-L-histidinyl]-(2S,3R,4S)-1-cyclohexyl-3,4-dihydroxy-6-(2-pyridyl)-2-hexylamide The title compound is prepared from the compound from Example 25 by the process stated in Example 2.

MS (FAB):752 (M+H)

EXAMPLE 27

N-[N-(3(N-Benzyl-piperidinyl-4-amioncarbonyl)-2(R)-(1-naphthylmethyl)-propionyl)-L-histidinyl]-(2S,3R,4S)-1-cyclohexyl-3,4-dihydroxy-6-(2-pyridyl)-2-hexylamide The title compound is prepared from the compound from Example 27a by the process stated in Example 1.

MS (FAB):842 (M+H)

a)

N-[N-(2(R)-(3-Benzyl-piperidinyl-4-aminocarbonyl)-1-naphthylmethyl)-propionyl)-L-histidinyl(DNP)]-(2S,3R,4S)-1-cyclohexyl-3,4-dihydroxy-6-(2-pyridyl)-2-hexylamide The title compound is prepared from the compounds from Examples 1f and 27b by the process stated in Example 1a.

MS (FAB:1008 (M+H)

b)

2(R)-[3-(N-Benzyl-piperidinyl-4-aminocarbonyl)-1-naphthylmethyl]-propionic acid

The title compound is prepared from the compound from Example 27c by the process detailed in Example 5b.

MS (DCI):431 (M+H)

c) Benzyl 2(R)-[3-(N-benzyl-piperidinyl-4-aminocarbonyl)-1-naphthymethyl]-propionate The title compound is prepared from 4-amino-N-benzyl-piperidine and benzyl 2(R)-(carboxymethyl)-3-(1-naphthyl)propionate by the process stated in Example 1c.

MS (DCI):521 (M+H)

EXAMPLE 28

N-[N-(2(R)-(1-Naphthylmethyl)-3-(piperidinyl-4-aminocarbonyl)propionyl)-L-histidinyl]-(2S,3R,4S)-1-cyclohexyl-3,4-dihydroxy-6-(2-pyridyl)-2-hexylamide acetate The title compound is prepared from the compound from Example 27 by the process stated in Example 6.

MS (FAB):752 (M+H)

EXAMPLE 29

N-[N-(2(S)-Benzyl-3-(4-tert.-butyloxycarbonyl)amino-1-piperidinyl-sulfonyl)-propionyl)-L-histidinyl]-(2S,3R,4S)-1-cyclohexyl-3,4-dihydroxy-6-(2-pyridyl)-2-hexylamide The title compound is prepared from the compound from Example 29a in analogy to the procedure described in Example 1.

MS (FAB):838 (M+H)

a)

N-[N(2(S)-Benzyl-3-(4-(tert.-butyloxycarbonyl)amino-1piperidinyl-sulfonyl)-propionyl)-L-histidinyl(DNP)]-(2S,3R,4S)-1-cycohexyl-3,4-dihydroxy-6-(2-pyridyl)-2-hexylamide The title compound is prepared, for example, by the process of Example 1a from 2(R,S)-benzyl-3-[4-(tert.-butyloxycarbonyl)amino-1-piperidinyl-sulfonyl]-propionic acid. The two diastereomers which result are separated by column chromatography on silica gel using a 96/4 to 9/1 mixture of methylene chloride and methanol a solvent. The produce which is eluted first has an optical rotation of $[\alpha]_D^{20} = -35.9°$ (c=1, CH$_3$OH) and the produce eluted subsequently has a rotation of $[\alpha]_D^{20} = -24.8°$ (c=1, CH$_3$OH). One of the two diastereomers is the title compound.

MS (FAB)):1004 (M+H)

b)

2(R,S)-Benzyl)-3-[4-(tert.-butyloxycarbonyl)amino-1-piperidinyl-sulfonyl]-propionic acid Benzyl 2-(R,S)-benzyl-3-chlorosulfonyl-propionate is prepared in analogy to EP-A 236,734. Monobenzyl benzylmalonate is used in place of monoethyl benzylmalonate. 4-tert.-butyloxycarbonyl-amino-piperidine (2 mmol) and triethylamine (2 mmol) in 5.4 ml of methylene chloride are added to the chlorosulfonyl compound (2 mmol) in methylene chloride (3.2 ml) at −10° C. After the reaction (−15° C. for 15 min) and working up, 715 mg of sulfonamide derivative are obtained Melting point: 115°–117° C.

This substance is catalytically hydrogenated with Pd/C in methanol at room temperature, and the title compound is obtained.

Melting point: 161°–163° C.

MS (FAB):1004 (M+H)

EXAMPLE 30

N-[N-(3-(4-Amino-1-piperidinyl-sulfonyl)-2(R)-benzyl-propionyl)-L-histidinyl]-(2S,3R,4S)-1-cyclohexyl-3,4-dihydroxy-6-(2-pyridyl)-2-hexylamide acetate The title compound is prepared from the compound from Example 29 by the process of Example 2.

MS (FAB):738 (M+H)

EXAMPLE 31

N-[N-(2(R)-Benzyl-3-(4-(tert.-butyloxycarbonyl)aminomethyl-1-piperidinylcarbonyl)-propionyl)-L-histidinyl]-(2S,3R,4S)-1-cyclohexyl-3,4-dihydroxy-6-(2-pyridyl)-2-hexylamide The title compound is prepared from the compound from Example 31a by the process of Example 1.

MS (FAB):816 (M+H)

a)

N-[N-(2(R)-Benzyl-3-(4-(tert.-butyloxycarbonyl)aminomethyl-1-piperidinylcarbonyl)-propionyl)-L-histidinyl(DNP)]-(2S,3R,4S)-1-cyclohexyl-3,4-dihydroxy-6-(2-pyridyl)-2-hexylamide The title compound is prepared from the compounds from Examples 1f and 31b by the process of Example 1a.

MS (FAB):982 (M+H)

b)
2(R)-Benzyl-3-[4-(tert.-butyloxycarbonyl)aminomethyl-1-piperidinylcarbonyl]-propionic acid The title compound is prepared from the compound from Example 31c by the process stated in Example 1b.
MS (DCI):405 (M+H)

c)Benzyl 2(R)-benzyl-3-[4-(tert.-butyloxycarbonyl)aminomethyl-1-piperidinylcarbonyl]-propionate The title compound is prepared from benzyl (2R)-2(carboxymethyl)-3-phenylpropionate and the compound from Example 31d by the process detailed in Example 1c.
MS (DCI):495 (M+H)

d) 4-(tert.-Butyloxycarbonyl)aminomethyl-piperidine 10.8 g of 4-(aminomethyl)-piperidine are dissolved in 100 ml of $CH_2Cl_2$, 25 g of di-tert.-butyl dicarbonate are added, and the resulting solution is stirred at room temperature for 3 hours. The residue after concentration is taken up in diisopropyl ether and extracted twice with 100 ml of 5% strength $NaHSO_4$ solution each time, and the combined extracts are adjusted to pH 9 with $Na_2CO_3$ and extracted three times with 250 ml of EA. Drying over $Na_2SO_4$ and concentration in a rotary evaporator provides 6 g of the title compound as a colorless oil.
$R_f$(SiO$_2$, CH$_2$Cl$_2$/MeOH 9:1):0.12
MS (DCI):215 (M+H)

EXAMPLE 32

N-[N-(3-(4-Aminomethyl-1-piperidinyl-carbonyl)-2(R)-benzylpropionyl)-L-histidinyl]-(2S,3R,4S)-1-cyclohexyl-3,4-dihydroxy-6-(2-pyridyl)-2-hexylamide acetate This compound is prepared by the process detailed in Example 2 from the compound from Example 31; white amorphous solid.
MS (FAB):716 (M+H)

EXAMPLE 33

N-[N-(2(S)-(4-(tert.-Butyloxycarbonyl)aminomethyl-1-piperidinylcarbonyl-oxy)-3-phenyl-propionyl)-L-histidinyl]-(2S,3R,4S)-1-cyclohexyl-3,4-dihydroxy-6-(2-pyridyl)-2-hexylamide.

This compound is prepared from the compound from Example 33a by the process stated in Example 1.
MS (FAB):818 (M+H)

a)
N-[N-(2(S)-(4-tert.-Butyloxycarbonyl)aminomethyl-1-piperidinylcarbonyl-oxy)-3-phenyl-propionyl)-L-histidinyl(DNP)]-(2S,3R,4S)-1-cyclohexyl-3,4-dihydroxy-6-(2-pyridyl)-2-hexylamide.

The title compound is prepared by the process detailed in Example 1a from the compounds from Examples 1f and 33b; yellow resin.
MS (FAB):984 (M+H)

b)
2(S)-[4-(tert.-Butyloxycarbonyl)aminomethyl-1-piperidinyl-carbonyl-oxy]-3-phenyl-propionic acid This compound is prepared from the compound from Example 33c by the process of Example 3b.
MS (DCI):407 (M+H)

c) Ethyl 2(S)-[4-(tert.-butyloxycarbonyl)aminomethyl-1-piperidinyl-carbonyl-oxy]-3-phenyl-propionate This compound is prepared from ethyl 2(S)-hydroxy-3-phenyl-propionate and the compound from Example 31d by the process detailed in Example 3c.
MS (DCI):435 (M+H)

EXAMPLE 34

N-[N-(2(S)-(4-Aminomethyl-1-piperidinyl-carbonyl-oxy)-3-phenyl-propionyl)-L-histidinyl]-(2S,3R,4S)-1-cyclohexyl-3,4-dihydroxy-6-(2-pyridyl)-2-hexylamide acetate The title compound is prepared by the process detailed in Example 2 from the compound from Example 33; beige amorphous solid.
MS (FAB):718 (M+H)

EXAMPLE 35

N-[N-(R)-Benzyl-3-(4-(tert.-butyloxycarbonyl)amino-1-piperidinyl-carbonyl)-propionyl)-S-methyl-L-cysteinyl]-(2S,3R,4S)-1-cyclohexyl-3,4-dihydroxy-6-(2-pyridyl)-2-hexylamide 90.0 mg of the compound from Example 35a are stirred in 1 ml of $CH_2Cl_2$ with 600 µl of trifluoroacetic acid at room temperature for 4 h. The mixture is concentrated and codistilled with toluene and $CH_2Cl_2$, and the residue is taken up in EA and washed several times with 1N $NaHCO_3$ solution. Extraction by shaking with saturated brine and drying over $Na_2SO_4$ are followed by concentration. The resulting residue is dried under high vacuum and then dissolved in 3 ml of acetonitrile, and 67 mg of the compound from Example 1b, 26 mg of 1-hydroxybenzotriazole, 32 µl of N-ethylmorpholine and 68 mg of O-benzotriazol-1-yl-N,N,N',N'-tetramethyluronium hexafluorophosphate (HBTU) are successively added, and the solution is stirred at room temperature for 4 h. 5 ml of saturated brine are added to the solution, which is extracted three times with EA, and the combined EA extracts are washed twice with saturated NaCl solution and once with saturated brine. Drying over $Na_2SO_4$ and concentration are followed by chromatography on silica gel ($CH_2Cl_2$/MeOH 15:1). The result is 80 mg of the title compound as a pale beige resin.
$R_f$(SiO$_2$, CH$_2$Cl$_2$/MeOH 9:1):0.45
MS (FAB):782 (M+H), 804 (M+Na)

a) S-Methyl-L-cysteine (2S,3R,4S)-1-cyclohexyl-3,4-dihydroxy-6-(2-pyridyl)-2-hexylamide This compound is prepared from the compound from Example 1g and BOC-S-methyl-L-cysteine by the process stated in Example 1f.
MS (FAB):510 (M+H), 516 (M+Li)

EXAMPLE 36

N-[N-(3-(4-Amino-1-piperidinyl-carbonyl-2(R)-benzylpropionyl)-S-methyl-L-cysteinyl]-(2S,3R,4S)-1-cyclohexyl-3,4-dihydroxy-6-(2-pyridinyl)-2-hexylamide acetate The title compound is prepared from the compound from Example 35 by the process detailed in Example 2; pale yellow amorphous solid.
MS (FAB):682 (M+H), 704 (M+Na)

EXAMPLE 37

N-[N-(3-(4-tert.-butyloxycarbonyl)aminomethyl-1-piperidinyl-carbonyl)-2(R)-(1-naphthylmethyl)propionyl)-L-histidinyl]-(2S,3R,4S)-1-cyclohexyl-3,4-dihydroxy-6-(2-pyridyl)-2-hexylamide The title compound is prepared from the compound from Example 37a by the process of Example 1.
MS (FAB):866 (M+H)

a)

N-[N-(3-(4-tert.-Butyloxycarbonyl)aminomethyl-1-piperidinyl-carbonyl)-2(R)-(1-naphthylmethyl)propionyl)-L-histidinyl(DNP)]-(2S,3R,4S)-1-cyclohexyl-3,4-dihydroxy-6-(2-pyridyl)-2-hexylamide This compound is prepared from the compounds from Examples 1f and 37b by the process stated in Example 1a.
MS (FAB):1032 (M+H), 1038 (M+Li)

b)

3-[4-(tert.-Butyloxycarbonyl)aminomethyl-1-piperidinyl-carbonyl]-2(R)-(1-naphthylmethyl)-propionic acid This compound is prepared from the compound from Example 37c by the process of Example 1b.
MS (DCI):455 (M+H)

c) Benzyl 3-[4-(tert.-butyloxycarbonyl)aminomethyl-1-piperidinyl-carbonyl]-2(R)-(1-naphthylmethyl)-propionate This compound is prepared from benzyl 2(R)-(carboxy-methyl)-3-(1-naphthyl)-propionate and the compound from Example 1d by the process indicated in Example 1c.
MS (DCI): 545 (M+H)

EXAMPLE 38

N-[N-(3-(4-Aminomethyl-1-piperidinyl-carbonyl)-2(R)-(1-naphthylmethyl)-propionyl)-L-histidinyl]-(2S,3R,4S)-1-cyclohexyl-3,4-dihydroxy-6-(2-pyridyl)-2-hexylamide acetate The title compound is prepared from the compound from Example 37 by the process indicated in Example 2.
MS (FAB):766 (M+H)

EXAMPLE 39

N-[N-(3-(4-(tert.-Butyloxycarbonyl)amino-1-piperidinyl-carbonyl)-2(R)-(1-naphthylmethyl)propionyl)-S-methyl-L-cysteinyl]-(2S,3R,4S)-1-cyclohexyl-3,4-dihydroxy-6-(2-pyridyl)-2-hexylamide The title compound is prepared from the compounds of Examples 25b and 35a by the process detailed in Example 35.
MS (FAB):832 (M+H)

EXAMPLE 40

N-[N-(3-(4-Amino-1-piperidinyl-carbonyl)-2(R)-(1-naphthylmethyl)-propionyl)-S-methyl-L-cysteinyl]-(2S,3R,4S)-1-cyclohexyl-3,4-dihydroxy-6-(2-pyridyl)-2-hexylamide acetate The title compound is prepared from the compound from Example 39 by the process of Example 2.
MS (FAB):732 (M+H)

EXAMPLE 41

N-[N-(3-(4-(tert.-Butyloxycarbonyl)amino-1-piperidinyl-carbonyl)-2(R)-(1-tetrahydronaphthylmethyl)propionyl)-L-histidinyl]-(2S,3R,4S)-1-cyclohexyl-3,4-dihydro-6-(2-pyridyl)-2-hexylamide The title compound is prepared from the compound from Example 41a by the process of Example 1.
MS (FAB):856 (M+H)

a)

N-[N-(3-(4-(tert.-Butyloxycarbonyl)amino-1-piperidinyl-carbonyl)-2(R)-(1-tetrahydronaphthylmethyl)propionyl)-L-histidinyl(DNP)]-(2S,3R,4S)-1-cyclohexyl-3,4-dihydroxy-6-(2-pyridyl)-2-hexylamide This compound is prepared from the compounds of Examples 1f and 41b by the process indicated in Example 35.
MS (FAB):1022 (M+H)

b)

3-[4-(tert.-Butyloxycarbonyl)amino-1-piperidinyl-carbonyl]-2(R)-(1-tetrahydronaphthylmethyl)-propionic acid This compound is produced besides that from Example 25b from the compound from Example 25c by the process stated in Example 1b when the hydrogenation time is extended from 1 h to 24 h. The title compound is isolated by chromatography on silica gel ($CH_2Cl_2$/MeOH 95:5).
MS (DCI):445 (M+H)

EXAMPLE 42

N-[N-(3-(4-Amino-1-piperidinyl-carbonyl)-2(R)-(1-tetrahydronaphthylmethyl)propionyl)-L-histidinyl]-(2S,3R,4S)-cyclohexyl-3,4-dihydroxy-6-(2-pyridyl)-2-hexylamide acetate The title compound is prepared from the compound from Example 41 by the process detailed in Example 2.

EXAMPLE 43

N-[N-(2(R)-Benzyl-3-(4-tert.-butyloxycarbonyl)amino-2,6-dimethyl-1-piperidinyl-carbonyl)-propionyl)-L-histidinyl]-(2S,3R,4S)-1-cyclohexyl-3,4-dihydroxy-6-(2-pyridyl)-2-hexylamide The title compound is prepared from the compound from Example 43a by the process stated in Example 1.
MS (FAB):830 (M+H)

a)

N-[N-(2(R)-Benzyl-3-(4-(tert.-butyloxycarbonyl)amino-2,6-dimethyl-1-piperidinyl-carbonyl)-propionyl)-L-histidinyl(DNP)]-(2S,3R,4S)-1-cyclohexyl-3,4-dihydroxy-6-(2-pyridyl)-2-hexylamide The title compound is prepared from the compounds from Examples 1f and 43b by the process stated in Example 35.
MS (FAB):996 (M+H)

b)

2(R)-Benzyl-3-[4-tert.-butyloxycarbonyl)amino-2,6-dimethyl-1-piperidinyl-carbonyl]-propionic acid The title compound is prepared from the compound from Example 43c by the process detailed in Example 1b.

MS (DCI):419 (M+H)

c)

Benzyl2(R)-benzyl-3-[4-(tert.-butyloxycarbonyl)amino-2,6-dimethyl-1-piperidinyl-carbonyl]-propionate The title compound is prepared from benzyl (2R)-2-(carboxymethyl)-3-phenylpropionate and the compound from Example 43d by the process of Example 1c.
MS (DCI): 509 (M+H)

d)

4-(tert.-Butyloxycarbonyl)amino-2,6-dimethyl-piperidine

This compound is prepared from the compound from Example 43c by the process of Example 1d.
MS (DCI):229 (M+H)

e) 1-Benzyl-4-[(tert.-butyloxycarbonyl)amino]-2,6-dimethyl-piperidine

This compound is prepared from the compound from Example 43f by the process detailed in Example 1e.
MS (DCI):319 (M+H)

f) 4-Amino-1-benzyl-2,6-dimethyl-piperidine 5 g of the compound from Example 43g are dissolved in 10 ml of methanol, 2 ml of concentrated ammonia solution and Raney nickel are added and hydrogenation is carried out in an autoclave under a pressure of 100 atm. The mixture is filtered and concentrated, and the resulting residue is purified by distillation.
MS (DCI):219 (M+H)

g) 1-Benzyl-2,6-dimethyl-4-piperidone oxime 10 g of 1-benzyl-2,6-dimethyl-4-piperidone (prepared from benzylamine and ethyl crotonate in analogy to Bull. Chem. Soc. Japan 31 (1958) 418) are dissolved in 60 ml of methanol and this solution is added dropwise to a solution of 3.8 g of hydroxylamine hydrochloride and 4.5 g of sodium acetate in 150 ml of water. The mixture is stirred at 60° C. for 2 h and cooled to 0° C., and the oxime which has separated out is filtered off with suction. Drying results in 5.2 g of the title compound.
MS (DCI):233 (M+H)

EXAMPLE 44

N-[N-(3-(4-Amino-2,6-dimethyl-1-piperidinyl-carbonyl)-2(R)-benzyl-propionyl)-L-histidinyl]-(2S,3R,4S)-1cyclohexyl-3,4-dihydroxy-6-(2pyridyl)-2-hexylamide acetate The title compound is prepared from the compound from Example 43 by the process detailed in Example 2.
MS (FAB):730 (M+H)

EXAMPLE 45

N-[N-(2(S)-(4-tert.-Butyloxycarbonyl)amino-2,6-dimethyl-1-piperidinyl-carbonyl-oxy)-3-phenyl-propionyl]-L-histidinyl]-(2S,3R,4S)-1-cyclohexyl-3,4-dihydroxy-6-(2-pyridyl)-2-hexylamide The title compound is prepared from the compound from Example 45a by the process stated in Example 1.
MS (FAB):832 (M+H)

a)

N-[N-(2(S)-(4-(tert.-Butyloxycarbonyl)amino-2,6-dimethyl-1-piperidinyl-carbonyl-oxy)-3-phenyl-propionyl)-L-histidinyl(DNP)]-(2S,3R,4S)-1-cyclohexyl-3,4-dihydroxy-6-(2-pyridyl)-2-hexylamide The title compound is prepared from the compounds from Examples 1f and 45B by the process stated in Example 35.
MS (FAB):998 (M+H)

b)

2(S)-[4-(tert.-Butyloxycarbonyl)amino-2,6-dimethyl-1-piperidinyl-carbonyl-oxy]-3-phenyl-propionic acid This compound is prepared from the compound from Example 45c by the process of Example 3b.
MS (DCI):421 (M+H)

c) Ethyl 2(S)-[4-(tert.-Butyloxycarbonyl)amino-2,6-dimethyl-1-piperidinyl-carbonyl-oxy]-3-phenyl-propionate This compound is prepared from ethyl 2(S)-hydroxy-3-phenylpropionate and the compound from Example 43d and the process of Example 3c.
MS (DCI):449 (M+H)

EXAMPLE 46

N-[N-(2(S)-4-Amino-2,6-dimethyl-1-piperidinyl-carbonyl-oxy)-3-phenyl-propionyl)-L-histidinyl]-(2S,3R,4S)-1-cyclohexyl-3,4-dihydroxy-6-(2-pyridyl)-2-hexylamide acetate The title compound is prepared from the compound from Example 45 by the process stated in Example 2.
MS (FAB):732 (M+H)

We claim:
1. A compound of the formula I

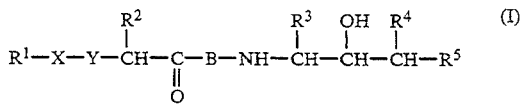

in which
R$^1$ is a radical of the formula II, III or IV

in which
R$^6$, R$^7$ and R$^8$ are identical or different and are hydrogen, (C$_1$–C$_4$)-alkanoyl, (C$_6$–C$_{12}$)-aryl-(C$_1$–C$_4$)-alkyl, (C$_7$–C$_{13}$)-aroyl, nicotinoyl (C$_1$–C$_4$)-alkoxycarbonyl or benzyloxycarbonyl;

$R^9$ is hydrogen, $(C_1-C_3)$-alkyl, $(C_4-C_6)$-cycloalkyl, $(C_4-C_6)$-cycloalkyl-$(C_1-C_2)$-alkyl, $(C_6-C_{12})$-aryl or $(C_6-C_{12})$-aryl-$(C_1-C_2)$-alkyl; and Z is —$CH_2$—;

X is —CO— or —$SO_2$—;

Y is —$CH_2$—$(CR^{13}R^{14})_r$— or —O— in which
r is 0 or 1; and
$R^{13}$ and $R^{14}$ are identical or different and are hydrogen, methyl or ethyl;

$R^2$ is cyclohexylmethyl, benzyl, 1- or 2-naphthylmethyl, 2-, 3- or 4-thienylmethyl, p-methoxybenzyl or p-fluorobenzyl;

$R^3$ is isobutyl, benzyl or cyclohexylmethyl;

$R^4$ is hydrogen or hydroxyl;

$R^5$ is a radical of the formula (V)

$(CH_2)_x$—$CHR^{15}$—Het     (V)

in which
$R^{15}$ is hydrogen or fluorine;

Het is a 2-, 3- or 4-pyridyl radical; and s is 0, 1 or 2; and

B is a radical of an amino acid H—B—OH, wherein said amino acid radical is phenylalanine, histidine, tyrosine, norvaline, norleucine or 5-methyl-cysteine;

or the physiologically tolerated salts thereof.

2. A compound of the formula I as claimed in claim 1, in which
$R^6$, $R^7$ and $R^8$ are identical or different and are hydrogen, acetyl, benzyl, benzoyl, nicotinoyl, tert.-butoxycarbonyl or benzyloxycarbonyl, and
$R^9$ is hydrogen or benzyl.

3. A compound of formula I as claimed in claim 1, in which
the radical B is histidine or norvaline.

4. A pharmaceutical composition comprising at least one compound of the formula I as claimed in claim 1 together with a pharmaceutically acceptable carrier.

* * * * *

UNITED STATES PATENT AND TRADEMARK OFFICE
CERTIFICATE OF CORRECTION

PATENT NO. : 5,374,731
DATED : December 20, 1994
INVENTOR(S) : Holger HEITSCH et al It is certified that error appears in the above-indentified patent and that said Letters Patent is hereby corrected as shown below:

Claim 1, Column 31, Lines 10-15 indent each one additional space; and

Claim 1, Column 31, in Formula (V) change "$(CH_2)x$" to --$(CH_2)s$--.

Signed and Sealed this

Thirtieth Day of May, 1995

Attest:

BRUCE LEHMAN

*Attesting Officer*  *Commissioner of Patents and Trademarks*